United States Patent [19]

Drummond

[11] Patent Number: 5,402,786

[45] Date of Patent: Apr. 4, 1995

[54] MAGNETO-ACOUSTIC RESONANCE IMAGING

[75] Inventor: James E. Drummond, P.O. Box 107, Lincoln City, Oreg. 97367

[73] Assignees: James E. Drummond; Joy T. Drummond, both of Otis, Oreg.

[21] Appl. No.: 943,551

[22] Filed: Sep. 11, 1992

[51] Int. Cl.⁶ .............................................. A61B 5/055
[52] U.S. Cl. ............................ 128/653.2; 128/660.01; 324/318
[58] Field of Search ............ 128/653.2, 653.5, 660.01, 128/660.02, 653.1; 324/318, 322

[56] References Cited

U.S. PATENT DOCUMENTS 4,543,959 10/1985 Sepponen .......................... 128/653.2
4,558,425 12/1985 Yamamoto et al. ................. 324/313

Primary Examiner—Ruth S. Smith
Attorney, Agent, or Firm—Benman, Collins & Sawyer

[57] ABSTRACT

A less expensive apparatus and associated method for Magnetic Resonance Imaging (MRI) of body tissues are disclosed. A physician uses an ultrasonic detector in combination with a weak magnetic field and pulsed, low frequency R.F. generator. The patient lies partially within the field of a magnet and receives low frequency radio pulses. As is shown below, ultrasonic waves are produced within the patient's body by the ordinary occurrence of nuclear magnetic resonance. For this reason, ultrasonic acoustic detection replaces the usual radio detection of the magnetic resonance induced spin echoes. The physician manipulates a hand-held ultrasonic detector with real time image feedback in much the same way that an ultrasonic transducer is used to provide the usual ultrasonic images. In the present case, however, no ultrasonic waves are emitted by the transducer; instead, the waves emitted by the "slice" selected by the radio frequency resonance with tissue protons are the source of the ultrasonic image produced. The MRI advantages of image production emphasizing longitudinal, T1, spin relaxation or transverse, T2, relaxation are retained. The usual problem that MRI has in low-noise measurement and location of spin echoes is obviated by the intrinsic ability to locate possessed by short wavelength ultrasonic signals. The need for very high magnetic fields in MRI to improve signal-to-noise ratio is removed in the present system. This removes a large capital expense. Another capital expense required by MRI is its complex magnetic field pulsing equipment. Such equipment is necessary to locate echoes using long wavelength R.F. detection. For a given frequency, of magnetic moment precession, the length of the acoustic waves, which are emitted at twice the precession frequency, are 100,000 times shorter than the length of radio waves, which are emitted at the precession frequency. Thus acoustic detection easily locates and measures the sources of magnetic spin echoes with a smaller burden of pulsed and steady magnetic fields.

16 Claims, 4 Drawing Sheets

MAGNETO-ACOUSTIC RESONANCE IMAGING

BACKGROUND OF THE INVENTION

1. Field of the Invention

The present invention relates to nuclear magnetic resonance equipment and process of using the equipment to produce magnetic spin echoes. It also relates to directional ultrasonic detection equipment.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

2. Description of Related Art

Sonography has been used as an independent comparison system in (MRI. (See "ECG-Triggered Magnetic Resonance Tomographic Measurement of Blood Flow Velocity in the Cartid Arteries: Comparison with Duplex Sonography" by M. Seiderer, K. Kroner, E. Muller, F. Spengel in Digitale-Bilddiagn, September 1988, pp. 110–114.). An ultrasonic wave or light beam system has also been used to adjust automatically the magnetic gradient for the size of an object to be examined by (MRI. (See U. S. Pat. No. 4,558,425, entitled "NMR Imaging Apparatus of Changeable Inspecting Zone Size", by Yamamoto-Etsuji et al. ). Another invention uses ultrasonics to find, localize and visualize the object to be examined by (MRI. (See "U. S. Pat. No. 4,543,959, entitled DIAGNOSIS APPARATUS AND THE DETERMINATION OF TISSUE STRUCTURE AND QUALITY, issued Oct. 1, 1985 to Sepponen.). In these cases the usual ultrasonic pulse ranging and pointing procedures were used to help MRI equipment fix on a region of interest, but then the MRI equipment proceeded with its usual series of transmitter, field, and receiver pulsing sequences. (See "Ultrasound: Basic Principles", by R. Price, T. Jones, A. Fleischer and A. E. James, Jr., Chapters 12 and 13 in *The Physical Basis of Medical Imaging*, by C. M. Coulam et al., ed. Appleton-Century-Crofts, 1981. See also "The MRI Manual", Ch. 1, Yearbook Medical Publishers, 1990.). Position along one axis is encoded by measuring phase change which occurs during an interval when a spatial gradient field is pulsed on. Position along an orthogonal axis is measured by the precession frequency at a later interval when another gradient is pulsed on during reception of the spin echoes. In order to get reasonable accuracy, a variety of delay intervals are used in the phase measurement. This not only results in long total diagnostic time;, but signal decay proceeds during the delay due to irreversible, statistical losses of time constant T2. (See "The Origins and Future of Nuclear Magnetic Resonance Imaging", by F. W. Wehrli, Physics Today 45.). This decreases the signal-to-noise ratio. Since signal-to-noise ratio is directly proportional to magnetic field strength, the trend has been to higher fields. This builds in expense growth well beyond normal medical cost inflation. What is needed, is a system to locate and measure the spin resonance echoes without having to pulse magnetic gradients in high overall fields.

Nuclear spins interact with sound waves at twice the Larmor precession frequency as is shown by observed Raman Scattering. (See also, "Physical Electronics", by D. I. Bolef, Academic Press, vol. 4, 1965 and "Proceeding of I.E.E.E.", by D. I. Bolef and R. R. Sundfors, vol. 53, p. 1574, 1975 and "Soviet Physics Acoustics", by V. V. Shutilov, vol. 8 p. 303, 1963.). Application of a 25.33 MHz ultrasonic wave to $KMnF_3$ caused transitions in the $F^{19}$ nuclear magnetic resonance spectral line. (See "Physics Review Letters", by A Dennison, et al, vol. 12, p. 244, 1964.). Interferometry of optical signals, reflected from compressed wave-guides have been used to enhance sensitivity to ultrasonic signals. (See U. S. Pat. No. 4,959,539, entitled FLEXURAL DISK FIBER OPTIC HYDROPHONE, issued Sept. 25, 1990 to Hofler et al.).

SUMMARY OF INVENTION

The need for an alternative method of location and measurement of resonance-induced spin precession is addressed by the present invention. The method of examination is the following:

1. Produce within the body of a patient a steady magnetic gradient like that produced with ordinary MRI for "slice" selection.
2. Use a "90°" tuned R.F. pulse to cause a large, coherent, precession of nuclear magnetic moments transverse to the magnetic field within the selected "slice" as is done with ordinary MRI. The reversible Free Inductive Decay (FID) occurs with a time constant T2* because of the mixture of precession frequencies in the magnetic gradient within the "slice".
3. Wait for an interval, TE/2, dependent only upon optimizing image contrast with respect to T2.
4. Produce a "180°" R.F. pulse to reverse phases attained by precessing magnetic moments during TE/2 as with ordinary MRI.
5. At about TE begin to scan the "slice" with the directional ultrasonic detector. Many voxels can be measured during the total echo interval, 2.T2*.
6. Repeat the above sequence for a variety of intervals TR. This will allow effects due to longitudinal relaxation of spins, T1, to be measured.

Radio waves of less that 100 MHz are far to long to be used alone to identify the origin of signals within the body. As a result, clever position coding schemes have been used but at a cost in capital equipment and/or signal-to-noise ratio.

DESCRIPTION OF THE INVENTION

Figure 1:
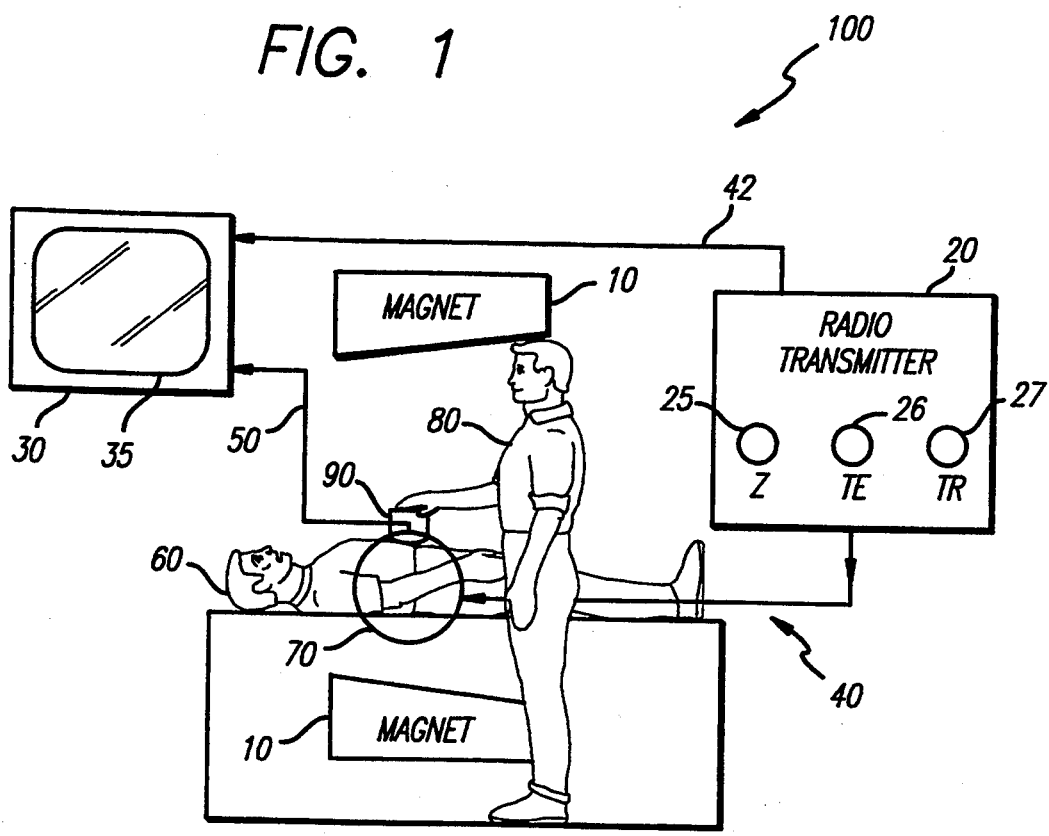
FIG. 1 shows an overall view of an illustrative implementation of a Magneto-Acoustic Resonance Imaging diagnostic system constructed according to the teachings of the present invention.

The invented apparatus shown at 100 in FIG. 1 contains a pulsed RF generator, 20, producing magnetic fields through coil 70 via cable 40. The location, Z, of the resonant "slice" along the direction of the magnetic gradient is chosen by setting control 25 which adjusts the frequency of the R.F. generator to resonate with protons at Z within the patient 60. The magnetic field, H, preferably of the order of 0.01 tesla, and its gradient are produced by magnets 10. The intensity and duration of the first R.F. pulse are such as to increase the transverse magnetization and coherence of the precessing nuclear spins. For an intensity $H_1 << H$ of resonant R.F. magnetic field, the time, $t_{90}$, to tip the spins 90° is $$t_{90} = \tfrac{1}{4} g H_1 \tag{1}$$

where g is the gyromagnetic ratio for protons=42.58 MHz/tesla. (See "Magnetic Resonance", by D. Ames, in *Handbook of Physics*, by E. Condon & H. Odishaw, p. 8-116, McGraw-Hill, 2nd ed., 1967.).

In order to see the effects of the transverse attenuation time constant, T2, the time delay to the echo is chosen by control 26. This causes a second R.F. pulse (the 180° pulse), twice as long as the first pulse, to occur at TE/2 after the first pulse. The second pulse reverses the phases of all precessing spins. These spins have slightly different precessional frequencies due to the slightly different magnetic fields across the thickness of the "slice". As a result they get out of phase with one another during TE/2. After the phases are reversed, these spins begin to coalesce in phase for the next interval of TE/2 forming a spin echo after a total period of TE.

Figure 2:
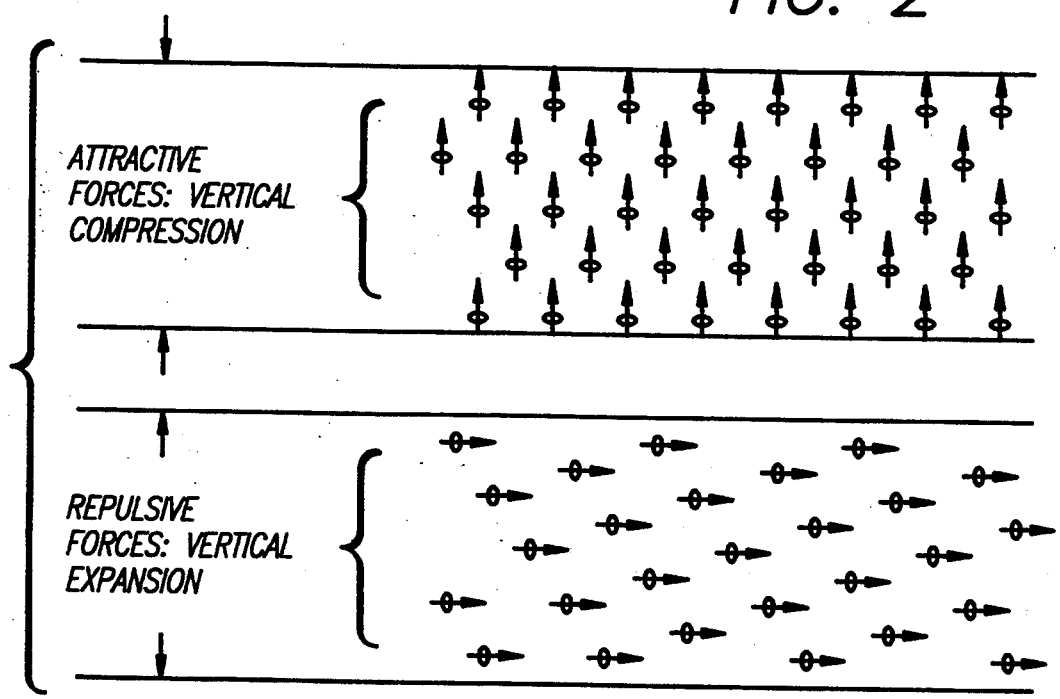
FIG. 2 schematically illustrates coherent spins within a "slice" at two times separated by 90° of the Larmor precession period.

When the phases have coalesced, their projections on the plane transverse to the main magnetic field would look something like the array of vectors shown in FIG. 2. At one instant they would all be pointing in a given direction; a moment later they would all be pointing at right angles to that direction; a moment later still they will have reversed from their original direction; and so on. The frequency with which they precess is the Larmor frequency:

$$f = g \cdot H \tag{2}$$

Magnetic moments attract each other along their axes and repel each other transverse to their axes. This may be seen immediately because opposite poles attract and like poles repel. To get a rough measure of the attraction or repulsion, we calculate the magnetic field at a position r from a proton magnetic moment m. (See, for example, "Magnetism", in *Van Nostrond's, Scientific Encyclopedia*, 6 Ed., pp. 1804-5, 1983.).

$$H(r) = -\nabla \frac{m \cdot r}{r^3} = -\frac{m}{r^3} + 3r \frac{m \cdot r}{r^5} \tag{3}$$

where the magnitude of $m = 1.41 \cdot 10^{-26}$ amp m² for protons. The interaction energy of another magnetic dipole at r with this magnetic field is $$W(r) = -\mu m \cdot H = \frac{\mu m^2}{r^3} [1 - 3\cos^2(\phi)] \tag{4}$$

where $\phi = 2\pi f t$ is the angle between the direction of the moments and the direction, r, from one proton to the other. The stretching force experienced by the molecule to which a nuclear spin is attached is the negative gradient of this energy with respect to r, the distance between the moments:

$$\text{force} = -\frac{\partial W}{\partial r} = \tag{5}$$

$$\frac{3\mu m^2}{r^4} [3\cos^2(\phi) - 1] = \frac{3\mu m^2}{2r^4} [3\cos(2\phi) + 1]$$

This is equivalent to a pressure applied to each molecule making up the surface of the "slice". The magnitude of this pressure is given approximately by dividing f by r², the average area taken up by a water molecule of the surface of the "slice" where r is the average distance between protons in water.

$$p = \frac{\text{force}}{r^2} = \frac{3\mu m^2}{2r^6} [3\cos(2\phi) + 1] \tag{6}$$

It is instructive to evaluate the approximate magnitude of the double frequency component of this pressure. Using $\mu = 4\pi \cdot 10^{-7}$ henries/meter and $r = 1.5 \cdot 10^{-10}$ meters we get $$p_{2f} = 100 \text{ Pa} \tag{7}$$

The acoustic power flux associated with this is $$I = 0.5 \ (p_{2f})^2 / c\rho 3 \ mW/m^2 \tag{8}$$

where $c = 1500$ m/s, the speed of sound in soft body tissue and $\rho = 10^3$ kg/m³ is the density.

For comparison, the power flux emitted by diagnostic ultrasonic instruments is about 25 mW/cm₂. Ultrasonic reflectivities between soft tissues are of the order of 1%. (See "Ultrasound: Basic Principles" by R. Price et al., in *The Physical Basis of Medical Imaging* by C. Coulam et al., Appleton-Century-Crofts, 1981.). That means that typical intensity of ultrasound reflected toward the receiving transducer is of the order of 250 μW/cm². This is about a thousand times larger than the intensity emitted by the resonant "slice". Thus a more sensitive hydrophone must be used.

Figure 3:
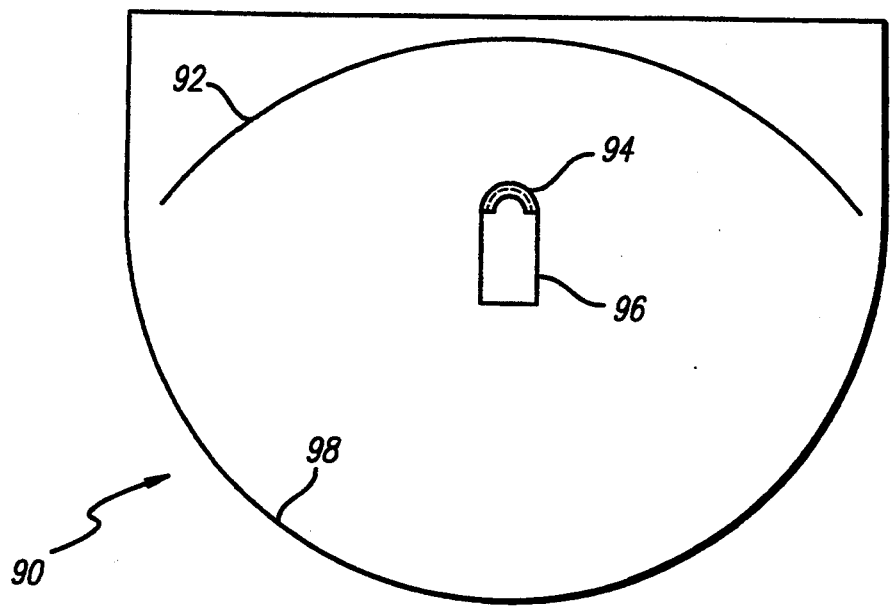
FIG. 3 shows a directional ultrasonic detector suitable for measurement of waves produced at twice the Larmor frequency by coherent spin echoes within the resonant "slice".
Figure 4:
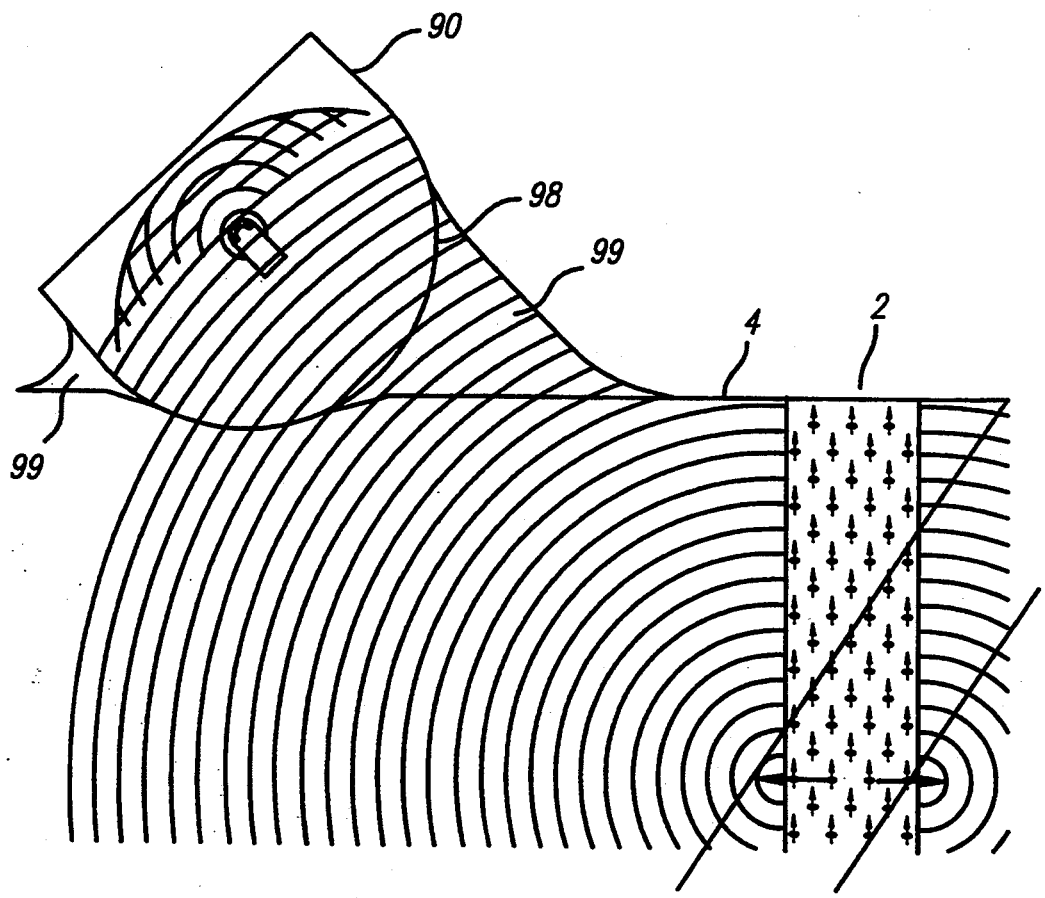
FIG. 4 shows one of many ultrasonic waves emitted by volume elements within a resonant "slice" impinging upon the ultrasonic transducer.

A concentrating hydrophone is illustrated at 90 in FIGS. 1, 3, and 4. FIG. 4 shows the hydrophone window, 98, at the surface of a patient's skin, 4, pointed toward a particular region of the "slice", 2, of precessing protons within the patient. Of all the sound waves emitted by all the regions of the "slice", only waves from this region are focused by the reflector 92 onto the sensor, 94. This focusing is aided by a gel, 99, clinging to the hydrophone and to the patient's skin as is commonly used to promote ultrasonic transmission between patients and transducers. The interior of the hydrophone 90 is preferably filled with water to conduct the ultrasonic waves with little change in acoustic impedance or speed from those parameters within the body. The reflector, 92, as shown in FIG. 3, is a rigid material preferably formed as a parabola of revolution reflecting ultrasonic waves onto the sensor, 94. For a diameter ratio of about 10:1 between this reflector and the sensor, the acoustic pressure intensification factor is 10:1 (power intensification factor, 100:1). For the case where the acoustic pressure at the "slice" is 100 Pa on a 1 cm diameter radiating area, the pressure at the sensor when the reflector is 10 cm from the acoustic source is 16 Pa. The shape of the reflector not only concentrates the ultrasonic waves, but maintains the phase relations so that waves from the axial direction of the parabola arrive in phase at the focus of the parabola. Waves from other directions arrive little concentrated and out of phase and so do not contribute significantly to a coherent acoustic pressure on the exposed surface of the sensor. The other surface of the sensor is bonded to support solid, 96. Solid 96, Supported by struts not shown, is such as to reflect the pressure wave it receives from the sensor 94, thus producing a standing wave within sensor 94. Thus the sensor 94 is preferably less than half a wavelength so that all parts of it experience the same phase of the pressure oscillations. The sensor 94 is made up of glass, single mode optical wave-guide wound over the outer edges on an interior, hemispherical core preferably of about 0.7 cm diameter to minimize optical losses due to curvature. With its cladding, the optical guide diameter is preferably about 26 $\mu$m. One end of this waveguide is reflectively terminated, the other is led out of the sphere and along one of the struts and through a water-tight port to a standard Michelson interferometer in unit 30. The length of guide within the annular volume between the core and the outside of the sensor is then about 160 m.

Figure 5:
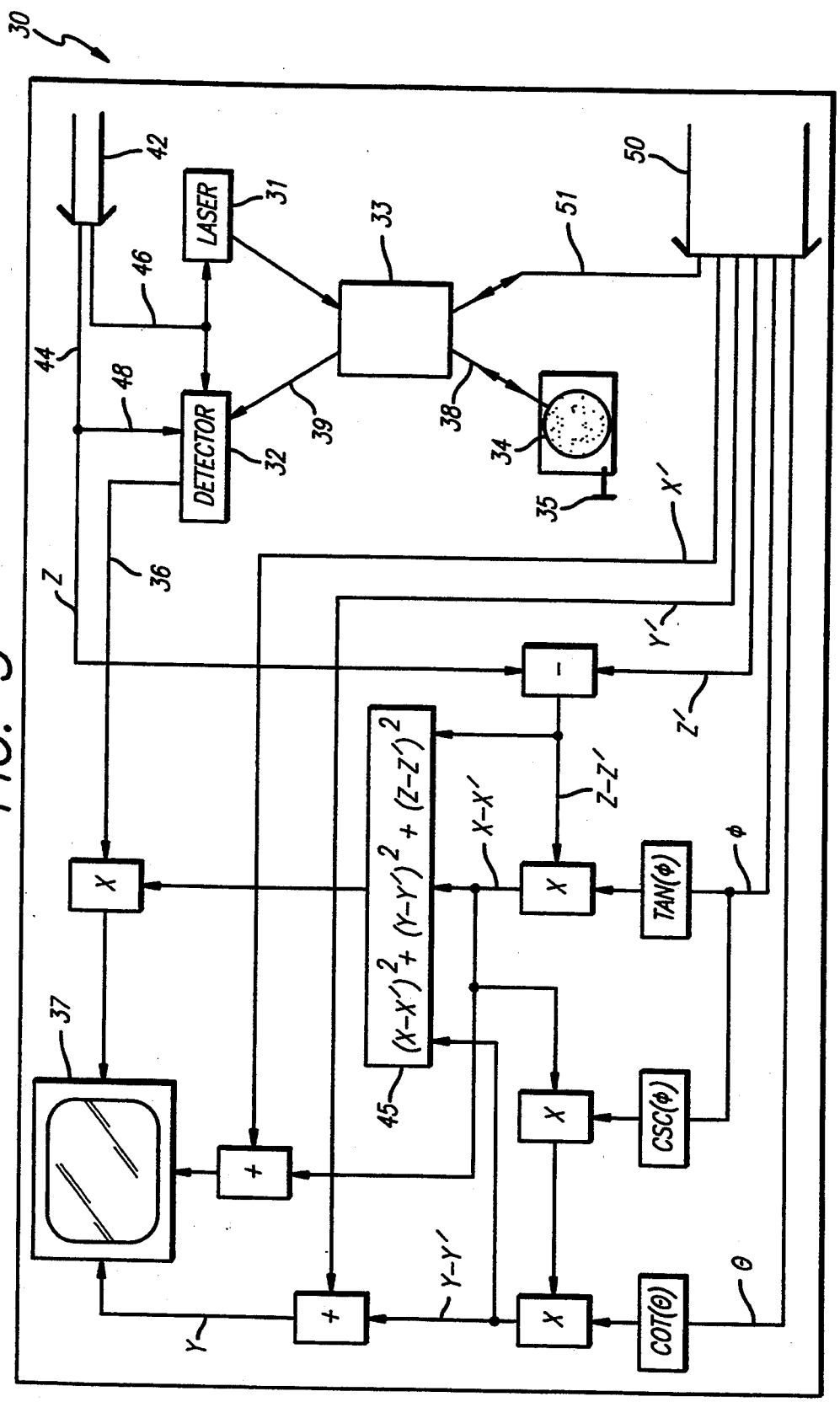
FIG. 5 provides a block diagram of an illustrative implementation the data receiving and imaging apparatus.
Figure 6:
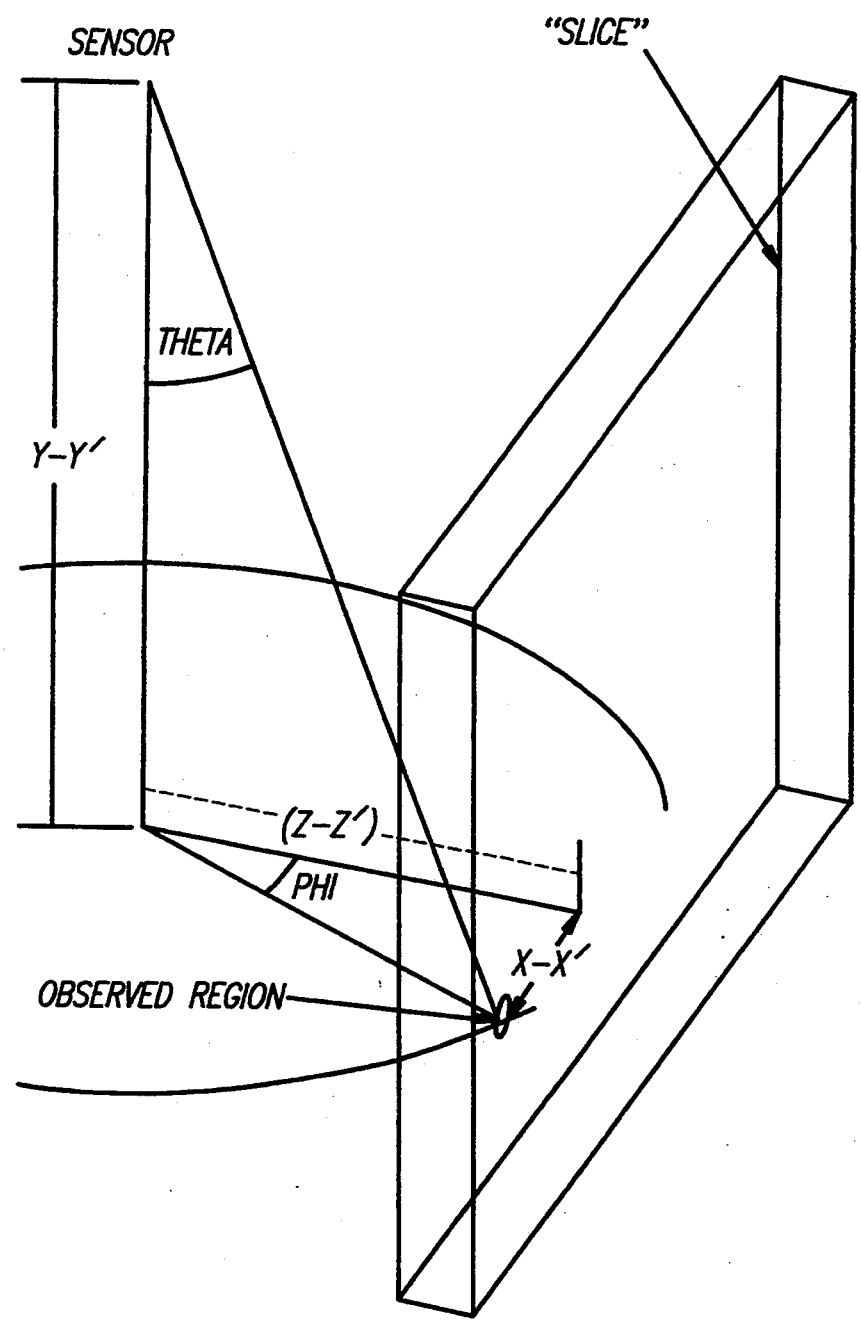
FIG. 6 shows the geometric relationships between the angles of the hydrophone and the location of the region of the "slice" under observation.

Matching boundary conditions for the acoustic wave in water and in fused silica glass gives a magnitude for acoustic pressure in the glass of 0.18 times its value in the water or p=2.9 Pa. This wave reflects front support 96. Choosing a material that has a good reflection coefficient, for example aluminum, provides increased acoustic pressure in the glass. The amplitude reflection at the glass-aluminum boundary is 0.92. The reflected wave will again be reflected at the glass-water interface with a reflected amplitude of 0.37. Multiple reflections will increase the acoustic pressure within the glass to 8.4 Pa. We must average this pressure over the fraction of a wavelength standing within the glass. If we take 0.01 T as the magnetic field, the Larmor frequency will be 426 KHz and the acoustic radiation will be at 852 kHz. The speed of sound in fused silica is 5.97 Km/s so the wavelength is 7 mm. Thus the 0.3 mm thickness of glass will support only 15° of standing wave so the spatial average differs negligibly from spatial maximum, This pressure on the optical guide, for which Poisson's ratio is $\sigma=0.17$, causes a fractional length decrease of $$\epsilon = p \cdot (1 - 2\sigma)/Y = 7.6 \cdot 10^{-11} \quad (9)$$

where Y is Young's modulus=$7.3 \cdot 10^{10}$ Pa for fused silica glass. For the 160 meter length, this represents a length change of $1.2 \cdot 10^{-8}$ m. This means a phase change of 7.2° in 0.82 $\mu$m light reflected from the end of the guide and measured in a standard Michelson interferometer. This wavelength is convenient because it is that of a popular diode laser. The optical signal passes through light guide 51 inside cable 50 to measurement unit 30 shown in FIG. 5. There, this light guide melds with light guide 38 in the 3 dB coupler, 33. Both these guides receive and reflect light from laser 31. The acoustically isolated, water filled, pressure chamber 34 contains a coil of waveguide comparable with that in the sensor 94. The two reflected waves merge in coupler 33 and are carried together in light pipe 39 to detector 32. The water filled pressure chamber 34 is fitted with pressure adjusting screw 35. This allows the wave in light pipe 38 to be adjusted to be 180° out of phase with that coming through light guide 51 in the absence of resonant nuclear spins. When an acoustic wave from nuclear spins is being received by sensor 94, this cancelation will be upset and an output, preferably square law signal will be produced and amplified. The amplifier can be tuned to the emitted acoustic frequency through input of the position, Z, by line 48. The envelope of the detected resultant signal, which follows the magnitude of the acoustic intensity, is sent via cable 36 and a multiplier, x, to the intensity input of the display unit, 37. The multiplicand, provided by unit 45, is the square of the distance from the sensor to the region it is focused upon. The position coordinates and angles of the hydrophone, controlled by physician 80, are encoded by standard electromechanical means and sent to the measurement unit by conductors labeled Y', X', Z', $\Phi$ and $\Theta$ within cable 50. The Z position of the "slice" is sent by conductor 44 within cable 42 to the unit 30 from the setting, 25, in unit 20 along with gating signals on line 46. The difference, Z−Z' (formed by subtraction unit "−"), which is the distance between the Z axis position of the sensor 94 and the slice 2 is used to multiply tan($\Phi$). As may be seen from FIG. 5, this reproduces the distance, X−X' which, added to X' in adder "+", is used to control horizontal position in the display unit 37. Multiplying this by csc($\Phi$) produces the cylindrical radius to the observed region. Multiplying the result by cot($\Theta$) yields Y−Y'. This, along with X−X' and Z−Z' is an input to unit 45 and, added to Y', it controls the vertical position of the display 37. These operations reproduce the coordinates X and Y on which the sensor 94 is focused and drive the horizontal and vertical positions of the display unit 37. The square of the distance between the sensor and the region upon which it is focused multiplies the measured sound intensity in order to supply a distance-independent value to the intensity axis of the image generation unit 37. The images thus generated are available instantly and are preferably electronically recorded by standard means (not shown) as well for later examination with a variety of standard image analyzing tools. Part of this analysis will normally consist of comparisons between images taken with a variety of repetition times, TR set by, control 27, which influence the magnitude of the spin echoes depending upon T1. Both T2 and T1 thus play important roles in forming contrast in the images.

It is evident that the fixed focus reflector of the embodiment shown in FIG. 3 could be modified by controlling the pressure difference between the front and back surfaces of the reflector, 92. This can be accomplished by sealing these two spaces from each other and supplying a distorting stress to the housing in back of reflector 92. The reflector will distort smoothly because of the fluid within the regions. A pressure gauge attached to the back region would be able to read a pre-calibrated focal distance so the focal manipulation could be done by the physician.

One advantage that MRI has is that it can be sensitized to the flow of fluids through the body. This is done by orienting a magnetic gradient along the course of vessels carrying the fluids. Then protons which Were not part of the resonant "slice" flow into the region under observation displacing resonating protons thus reducing the spin echo intensity in the region being observed. This can be used as well in the present invention. However, the fixed gradient of the embodiment shown in FIG. 1 would make it awkward to reorient the machine 6r patient for exploring a variety of flow directions. This need can be accomodated by supplying the steady magnetic field gradient with currents though coils where the currents can be redistributed to produce a gradient in any desired direction. Furthermore, use of the focusing hydrophone described above would make is possible to identify and localize spin echoes carried out of the "slice" by fluid motions without the complexity of mixing information coding which occurs in MRI.

It is also evident that a combination of acoustic pointing and the usual frequency encoding by means of a pulsed magnetic gradient could be used. Also automatic scanning could be used to replace physician 80 if desired or needed. These and other simple modifications will be obvious to those skilled in the arts employed in this invention.

What is claimed is:

1. A magneto-acoustic resonance instrument comprising:
   first means for producing nuclear spin echoes within a volume within a body and
   second means for measuring the intensity of a selected portion of said spin echoes, said means for measuring the intensity of a selected portion of said spin echoes, including means for sensing acoustic energy generated by said spin echoes.

2. The invention of claim 1 wherein said means for producing nuclear spin echoes includes magnetic means for producing a steady magnetic field along a given axis with a gradient orthogonal to said axis.

3. The invention of claim 2 wherein said means for producing nuclear spin echoes further includes means for producing an oscillating magnetic field orthogonal to said steady field.

4. The invention of claim 3 wherein said means for producing an oscillating magnetic field orthogonal to said steady field further includes a coil disposed in proximity to said body.

5. The invention of claim 4 wherein said means for producing an oscillating magnetic field orthogonal to said steady field further includes an oscillator for driving said coil.

6. The invention of claim 5 wherein said means for producing an oscillating magnetic field orthogonal to said steady field further includes means for driving said oscillator with a radio frequency signal.

7. The invention of claim 1 wherein said means for sensing acoustic energy generated by said spin echoes includes a directional hydrophone for sensing said acoustic energy and providing a first signal in response thereto.

8. The invention of claim 7 wherein said directional hydrophone includes a housing and an acoustic sensor disposed within said housing.

9. The invention of claim 8 wherein said directional hydrophone includes an acoustic focusing reflector for focusing energy on said sensor.

10. The invention of claim 9 wherein said housing is filled with liquid.

11. The invention of claim 10 wherein said housing has an acoustically transparent window.

12. The invention of claim 11 wherein said sensor comprises a reflectively terminated optical waveguide wrapped around a curved solid body.

13. The invention of claim 7 further including means for providing second signals indicative of the position of said volume within said body.

14. The invention of claim 13 further including means for displaying said first signals.

15. The invention of claim 14 further including means for displaying said first signals at positions on a display corresponding to said second signals.

16. A magneto-acoustic resonance measurement technique including the steps of:
   producing nuclear spin echoes within a narrow volume within a body,
   measuring the intensity of a selected portion of said spin echoes by sensing acoustic energy generated by said spin echoes.

* * * * *